United States Patent
Papaprodromou

(10) Patent No.: US 6,203,796 B1
(45) Date of Patent: Mar. 20, 2001

(54) OREGANO-BASED THERAPEUTIC COMPOSITION

(76) Inventor: Andreas D. Papaprodromou, 275 Norman Ave., Arcadia, CA (US) 91007

( * ) Notice: Subject to any disclaimer, the term of this patent is extended or adjusted under 35 U.S.C. 154(b) by 0 days.

(21) Appl. No.: 09/349,577

(22) Filed: Jul. 8, 1999

(51) Int. Cl.$^7$ .............................. A61K 35/78; A61K 9/00
(52) U.S. Cl. ...................... 424/195.1; 424/400; 514/817; 514/825; 514/886; 514/969
(58) Field of Search .................. 424/195.1, 400; 514/817, 825, 886, 969

(56) References Cited

U.S. PATENT DOCUMENTS

| | | |
|---|---|---|
| 1,298,407 | 3/1919 | Sams . |
| 3,067,103 | 12/1962 | Chen et al. . |
| 4,380,506 * | 4/1983 | Kimura et al. . |
| 4,883,664 | 11/1989 | Sharkey . |
| 5,017,397 * | 5/1991 | Nguyen et al. . |
| 5,073,366 | 12/1991 | Beck . |
| 5,080,901 | 1/1992 | Hangay et al. . |
| 5,091,379 | 2/1992 | Aungst . |
| 5,112,816 | 5/1992 | Narui et al. . |
| 5,124,320 | 6/1992 | Ivy et al. . |
| 5,223,257 | 6/1993 | Arora . |
| 5,599,561 | 2/1997 | Gonzalez, Jr. . |
| 5,674,853 | 10/1997 | Forse et al. . |
| 5,817,757 * | 2/1999 | Cloughley et al. . |
| 5,837,735 | 11/1998 | Miyata et al. . |

FOREIGN PATENT DOCUMENTS

| | | |
|---|---|---|
| 400395 * | 12/1995 | (AT) . |
| 2689011 * | 10/1993 | (FR) . |
| 1456275 | 11/1976 | (GB) . |
| 2224934 * | 12/1995 | (GB) . |

OTHER PUBLICATIONS

Ayoub, S. Planta Med. vol. 56 (6), pp. 644–645, abstract enclosed, 1990.*
Henry, T. Perfum. Essent. Oil Rec. vol. 1 (1), pp. 8–9, abstract enclosed, 1910.*
Barata et al. J. Essent. Oil Res. vol. 10(6), pp. 618–627, abstract enclosed, 1998.*
Regnaultroger et al. Acto Botanica Gall. vol. 140 (2), pp. 217–222, abstract enclosed, 1993.*
Aureli et al. J. Food Protect. vol. 55 (5), pp. 344–348, abstract enclosed, 1992.*
Zolfaghari et al. Iranian J. Med. Sci. vol. 22 (3–4), pp. 134–137, abstract enclosed, 1997.*
PDR for Herbal Medicines. 1$^{st}$ed. Publ. by Medical Economics Co. Montvale, NJ pp. 928–929, 987–988, 999–1000, 1004–1005. publ. Jan. 1998.*
World Wide Web, http://www.pennysaved.com/oregano.htm, *Wild Oil of Oregano, Oregamax Red Sour Grape & Hercules Strength* (1996).
World Wide Web, http://www.pagans.org/~atho/files/medical/OREGANO.TXT, *Origanum Vulgare* (1997).

* cited by examiner

*Primary Examiner*—Christopher Tate
(74) *Attorney, Agent, or Firm*—Sheldon & Mak

(57) ABSTRACT

A therapeutic composition comprising oregano oil, laurel oil, and myrtle oil useful in alleviating pain and discomfort associated with arthritis, migraines, bronchitis, soft tissue injuries, muscle aches and pains and neck and back pains and strains in humans, as well as upper respiratory, joint and shin ailments in animals.

21 Claims, 3 Drawing Sheets

OREGANO-BASED THERAPEUTIC COMPOSITION

BACKGROUND OF THE INVENTION

Natural herbs have been used for centuries to alleviate the deleterious effects of numerous types of ailments, as well as the pain and discomfort associated with these ailments. More recently, patents have been granted to herbal remedies that disclose novel combinations of herbs purported to relieve the pain and other debilitating effects of numerous ailments and disorders.

For instance, U.S. Pat. No. 1,298,407 teaches the use of a combination of natural herb oils and other ingredients for relief from catarrh, headache, toothache, sore throat, influenza, and colds. This herbal preparation purports to alleviate pain in the case of certain ailments.

Another example of an herbal remedy is taught in U.S. Pat. No. 3,067,103. Here the use of a *Gardenia florida* seed extract was reported to have enhanced healing properties when applied to soft tissue injuries.

A medical salve useful in treating burns was disclosed in U.S. Pat. No. 4,883,664 which included herbally-derived camphor and pine rosin.

In U.S. Pat. No. 5,073,366, an analgesic composition useful in providing temporary relief from the symptoms of arthritis was taught. This composition includes several herbally-derived substances, such as aloe vera gel, camphor, menthol, thymol, eugenol and eucalyptus oil.

Hangay et al, U.S. Pat. No. 5,080,901 teach the use of a composition containing plant extracts from marigold, horse-chestnut, licorice, silver-weed, walnut-tree leaves, lavender resinoid and camomile oil for ailments which exhibit inflammatory and skin irritating effects.

A topical composition for generally relieving aches and pains was disclosed in U.S. Pat. No. 5,223,257. This patent taught using wintergreen and eucalyptus oils, among other ingredients, as a remedy for many non-specific ailments.

However, despite the knowledge of herbal remedies gleamed from centuries of medicinal use, and despite the information publically disclosed in patents and other references, there is still a need for herbal remedies that can serve to give relief from the plethora of human and animal ailments, especially those that are accompanied by pain. Moreover, consumers desire herbal remedies to self-treat the discomfort and pain associated with numerous debilitating ailments.

Moreover, there appears to be no existing all herbal remedy that can quickly ameliorate the pain and discomfort associated with the many common ailments that so many people tolerate ever day, such as soft tissue injuries, arthritis, migraine headaches, bronchitis and non-specific muscular aches and neck and back pain. These commonplace ailments impair the quality of daily life for so many people. In this regard, medical science, with its reliance largely on synthetically manufactured pharmaceuticals, generally offers little assistance. Thus, there remains a need for a natural, all herbal remedy that can quickly and effectively alleviate the pain and discomfort associated with many commonplace ailments.

SUMMARY OF THE INVENTION

The present invention features an all herbal compositions useful as a topical therapy to relieve the pain and symptoms of numerous ailments in humans and animals. In particular, the therapeutic compositions of the present invention alleviate the pain and discomfort associated with human ailments, such as arthritis, bronchitis, migraine headaches, facial paralysis, soft tissue injuries, muscular aches and strains, and neck and back pain and strains. In animals, the compositions of the present invention relieve upper respiratory ailments, as well as joint and shin disorders.

There are generally three basic constituents of the all herbal compositions of the present invention. These constituents include an oil derived from oregano, an oil derived from laurel and an oil derived from myrtle. These essential oils are then combined to yield various therapeutic compositions.

Generally, each constituent oil can be varied within the total composition. For humans, the therapeutic composition includes about 60–95 percent oil of oregano, 3–20 percent oil of laurel and 0–15 percent oil of myrtle. For animal use, each constituent oil can be varied from about 35–100 percent volume of oregano oil, from about 0–20 percent volume of laurel oil and from about 0–35 percent volume myrtle oil. Additionally, olive oil can be added to the final mixture. Typically, this non-essential constituent of the therapeutic compositions of the present invention will comprise approximately 2–10 percent of the total volume of the therapeutic mixture. Moreover, the therapeutic compositions can be further combined with other emollients to yield herbal compositions in the form of a cream, lotion, ointment or salve.

Another aspect of the present invention features a method of making the therapeutic compositions. First, the appropriate plants are selected. For use in the present invention, oregano, laurel and myrtle grown in Cyprus, Crete or Greece are preferred. To derive the oil of oregano, all of the plant is used, that is, the leaves, the stems and the seed, whereas to derive the oils of laurel and myrtle, only the leaves are utilized. The overall protocols used to derived the essential oils of oregano, laurel and myrtle are generally either distillation or extraction. For either purification process, the plant matter from oregano, laurel or myrtle are first separately distilled or extracted and then combined in various ratios to yield the all herbal compositions of the present invention.

Finally, therapeutic uses for the all herbal compositions are included in the present invention. These uses include topically administering the therapeutic compositions to a person or animal in need by gently applying the oily mixture in the proximate area of discomfort. After waiting 5–20 minutes the therapeutic composition is then reapplied in the same manner.

DETAILED DESCRIPTION OF THE INVENTION

Figure 1:
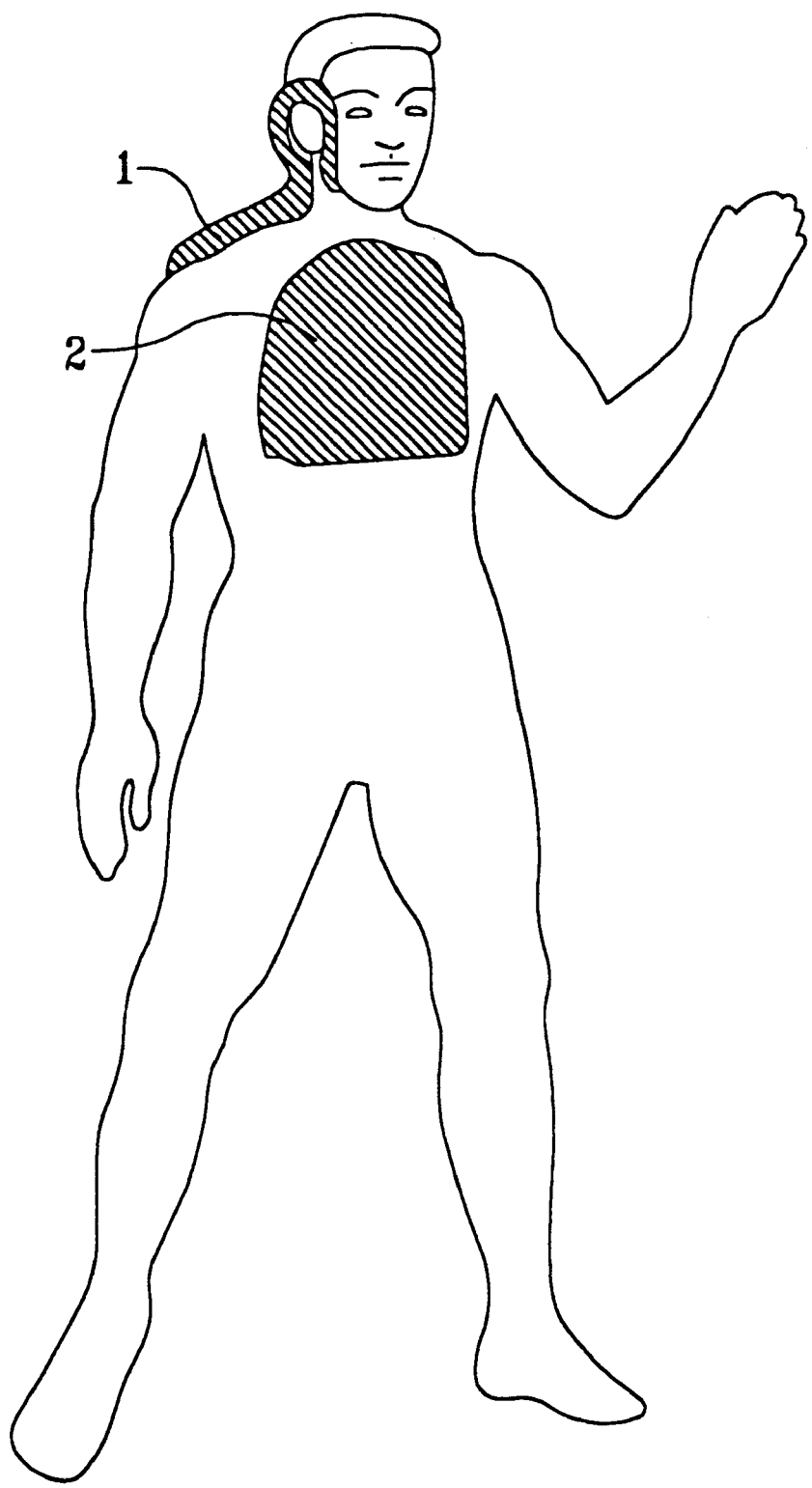
FIG. 1 illustrates the areas of human body to which compositions of the present invention are to be applied to alleviate bronchitis and facial paralysis.

The present invention involves a novel, all herbal composition useful as a therapeutic to alleviate the pain, discomfort and other associated symptoms related to human ailments, such as soft tissue injuries, arthritis, migraine headaches, bronchitis and non-specific muscular aches and neck and back pain, as well as upper respiratory, joint and shin ailments in animals.

The composition of the present invention includes three basic constituents or oils which are separately distilled or extracted, and then subsequently mixed to form the all herbal therapeutic composition. The basic constituents or oils for use in humans comprise: an oregano distillate or extract, a laurel distillate or extract and a myrtle distillate or extract. The relative amounts of the three constituents or oils of the therapeutic composition can vary from about 60–95 percent volume for the oregano distillate, from 3–20 percent volume for the laurel distillate and from about 0–1 5 percent volume for the myrtle distillate.

Olive oil is an optional component of the all herbal therapeutic composition. In the present invention, olive oil is useful mainly as a diluent for the distillate or extracted mixture and also aids in absorption of the composition through the skin. In this regard, other oils or emollients can be substituted for olive oil in the present invention. Further, the all herbal therapeutic composition, which yields an oily mixture or two or three distillates or extracts in the absence of olive oil, can be combined with any suitable other emollient, with or without the addition of olive oil.

Typical compositions in percent total volume are exemplified in the following table.

TABLE

| | Oil of Oregano | Oil of Laurel | Oil of Myrtle | Olive Oil |
| --- | --- | --- | --- | --- |
| 1 | 95 | 3 | 2 | — |
| 2 | 90 | 5 | 2 | 3 |
| 3 | 60 | 20 | 15 | 5 |
| 4 | 35 | 20 | 35 | 10 |
| 5 | 86 | 10 | 10 | — |
| 6 | 100 | — | — | — |
| 7 | 95 | 5 | — | — |

Compositions 1–3 listed in the above table are exemplified mixtures to be used with humans. Particular compositions are more suitable for particular applications as illustrated in the examples below. Compositions 4–5 are exemplified mixtures to be used with animals. Composition 6, which comprises only the oregano distillate, is suggested for use in animals, preferably horses. Composition 7 can be used in humans and animals.

Although the noted components may be the sole components of the composition, they can be optionally combined with a suitable carrier so that the resulting composition is in the form of a cream, lotion, ointment or salve. A suitable carrier for use with the composition of the present invention should be topically acceptable and compatible with the essential constituents. The carrier should also be chemically non-reactive with any of the essential constituents of the therapeutic composition. When a carrier is employed, it is advantageous for the resulting composition to be storage stable.

Since the present invention is derived from natural plant sources, which may vary from region to region around the world, in preparing the therapeutic composition of the present invention; the preferred source of each herbal oil is from the respective plant grown in Cyprus, Crete, and Greece. Oregano, laurel and myrtle plants grown in Cyprus, however, are most preferred for use in the present invention.

Oregano (*Origanum vulgare* L.), which is part of the lamiaceae or mint family, comprise several species. The most important species are *O. vulgare* (pan-European) *O. onites* (Greece Asia Minor) and *O. heracleoticum* (Italy, Balkan peninsula, West Asia). For use in the present invention, it is preferred that the oregano plant, regardless of plant species, be grown in Cyprus, Crete or Greece, with the plant grown in the mountains of Cyprus being most preferred. In preparing the therapeutic compositions of the present invention it is noteworthy that for the oil derived from the oregano plant, the influence of climate, season and soil on the resultant oil is greater than the differences between the various species.

The main constituents of oregano are an essential oil (maximum 4% of the leaves) which may contain variable amounts of phenols, carvacrol and thymol. Herein, "essential oil" means an oil derived by any means from a plant source. Additionally, a variety of monoterpene hydrocarbons, such as limonene, terpinene, ocimene, caryophyllene, beta-bisabolene and p-cymene, as well as monoterpene alcohols, such as linalool and 4-terpineol, have been reported to be part of the essential oil derived from the oregano plant. As noted above, the exact chemical composition of the essential oil derived from this plant will greatly depend on its geographical source.

Laurel (*Laurus nobilis* L.) is part of the Lauraceae or laurel family. The laurel tree, which grows throughout the Mediterranean region, comprises leaves and a fruit. The main constituents of the laurel plant is an essential oil derived from the leaves and comprising approximately 0.8% to 3% of the total weight of the leaves. This oil contains mostly 1,8 cineol, that is, approximately 50%. Additionally, the essential oil of the laurel plant may contain variable amounts of eugenol, acetyl eugenol, methyl eugenol, alpha-pinene, beta-pinene, phellandrene, linalool, geraniol and terpineol. Although not as critical to the resultant therapeutic composition of the present invention, as with oregano, it is preferred that the laurel plant be grown in Cyprus, Crete and Greece, with those plants grown in Cyprus being most preferred.

Myrtle is part of the Myrtaceae or myrtle family. The plant grows abundantly in the North Western to Eastern Mediterranean region and comprises leaves and berry fruits. The main constituents of the oil derived from myrtle leaves represents about 0.8% of the total weight of the leaves. This oil comprises mostly myrtenol and myrtenol acetate, with limonene (approximately 20% of the oil), pinene (approximately 14% of the oil), cineol (approximately 11% of the oil), and smaller amounts of p-cymene, geranio, nerol, and phenylpropane, methyleugenol comprising the remainder of the essential oil of the myrtle plant.

Olive oil is not an essential constituent, or oil, of the inventive therapeutic composition. However, where olive oil is to be used in a particular composition of the present invention, it is preferred that the oil be pure, virgin, naturally cold pressed olive oil.

The parts of the particular plant to be used in the present invention is also important to the overall quality of the final therapeutic composition. To produce the oil of oregano, all of the plant is used, namely the leaves, the stems and the seeds. In the case of oregano, the it is preferred that the plant be harvested between the months of May to October, when the plant produces flowers from which the seeds are derived. The preferred color of the oregano plant at the time of harvest, for use in the present invention, should be golden, and not green. Moreover, the leaves, stems and seeds of the oregano plant are to be dried, preferably sun dried, prior to use in the present invention. For the laurel and myrtle plants, only the green (not dried) leaves are suitable for use in preparing the novel therapeutic compositions. The laurel and myrtle leaves can be harvested any time of the year, as they are green all year round in the Mediterranean region.

Given that the appropriate herbal sources for preparation of the oregano distillate or extract have been located, the essential oils of the oregano, laurel and myrtle plants are then derived either by distillation or extraction. The preferred method of deriving the essential oil for use in the present invention, however, is distillation.

Regardless of the particular purification method utilized, each oil is derived by a separate process, and then subsequently mixed to obtain the therapeutic compositions of the present invention. As noted above, to obtain the oregano oil, the sun dried plant is used comprising the leaves, stems and seeds. To obtain both the laurel and myrtle oils, the green, i.e., not dried, leaves of the respective plants are used to prepare the therapeutic composition of the present invention.

The distillation protocol to be used in the present invention follows standard methods known in the art. For each distillation process, the appropriate starting material, that is the leaves, stems or seeds of the oregano plant, or the leaves of either the laurel or myrtle plant, is heated in water, preferably distilled water, for the appropriate amount of time and temperature to generate vapors which are subsequently cooled to form a liquid using any standard distillation apparatus. The amount of water used is not critical, but should be sufficient to completely immerse the plant material to be processed. The resultant liquid obtained via this distillation process is actually an oil and water mixture. The water is then allowed to evaporate at room temperature, leaving behind an oily substance containing the essential oil of oregano, laurel or myrtle.

For each extraction process, the appropriate material, that is the leaves, stems or seeds of the oregano plant, or the leaves of either the laurel or myrtle plant, are first heated in a minimum amount of water to cover the plant matter. The water is heated at 60 to 85 deg C. for one to three hours with stirring. The plant material is then removed from the water and placed in a mechanical pressing device where it is squeezed to extract any remaining liquid. This liquid is then added to the water which had been used to heat the plant material. If necessary, the resultant liquid can be left to evaporate to a smaller volume to facilitate the following extraction process. The final liquid is then extracted with an appropriate solvent. For the liquid derived from either the oregano, laurel or myrtle plant matter, these liquids may be preferably extracted with reagent grade ether. In preparing the laurel oil, chloroform may also be used for the extraction process.

The aqueous liquid should be extracted with a volume of organic solvent that is smaller than the aqueous liquid. Preferably, the organic solvent to aqueous liquid is approximately a ratio of 1:5 parts per volume. The aqueous liquid is then extracted at least three times with the organic solvent. Following extraction by any standard protocols known in the art, the solvent used, for instance ether, is allowed to evaporate leaving behind an oily substance containing the essential oil of oregano, laurel or myrtle.

The present invention has a myriad of therapeutic uses in treating certain human ailments. The all herbal composition is useful in alleviating the discomfort associated with arthritis, migraines, bronchitis, soft tissue injures, muscular aches and strains, and neck and back strains, as well as other uses, such as in alleviating the effects of certain kinds of facial paralysis. Moreover, different compositions comprising varying amount of oregano oil, laurel oil and myrtle oil are preferred in treating these different ailments.

Further, the compositions of the present invention are useful in treating ailments in animals, especially ailments that affect horses. For animal use, as with use in humans, different compositions comprising varying amount of oregano oil, laurel oil and myrtle oil are preferred in treating these different ailments.

Referring to the figures, FIG. 1 illustrates several applications of the therapeutic compositions of the present invention. For treatment of bronchitis 1 or facial paralysis 2, the area of the body to apply the all herbal compositions of the present invention is illustrated by the shaded areas in the figure. For bronchitis 1, the therapeutic composition preferably comprising 60% oil of oregano, 20% oil of laurel, 15% oil of myrtle and 5% olive oil (Composition 3 from the Table) is gently applied to the chest area. After waiting 5–20 minutes the therapeutic composition is then reapplied in the same manner. For facial paralysis 2, the area of application starts on the affected area of the face and is followed around the ear area and downward along the shoulder, on the same side where the facial paralysis is apparent. As with bronchitis 1, for facial paralysis 2, the therapeutic composition preferably comprising 60% oil of oregano, 20% oil of laurel, 15% oil of myrtle and 5% olive oil (Composition 3 from the Table) is preferably gently applied to the illustrated areas. After waiting 5–20 minutes the therapeutic composition is then reapplied in the same manner.

Figure 2:
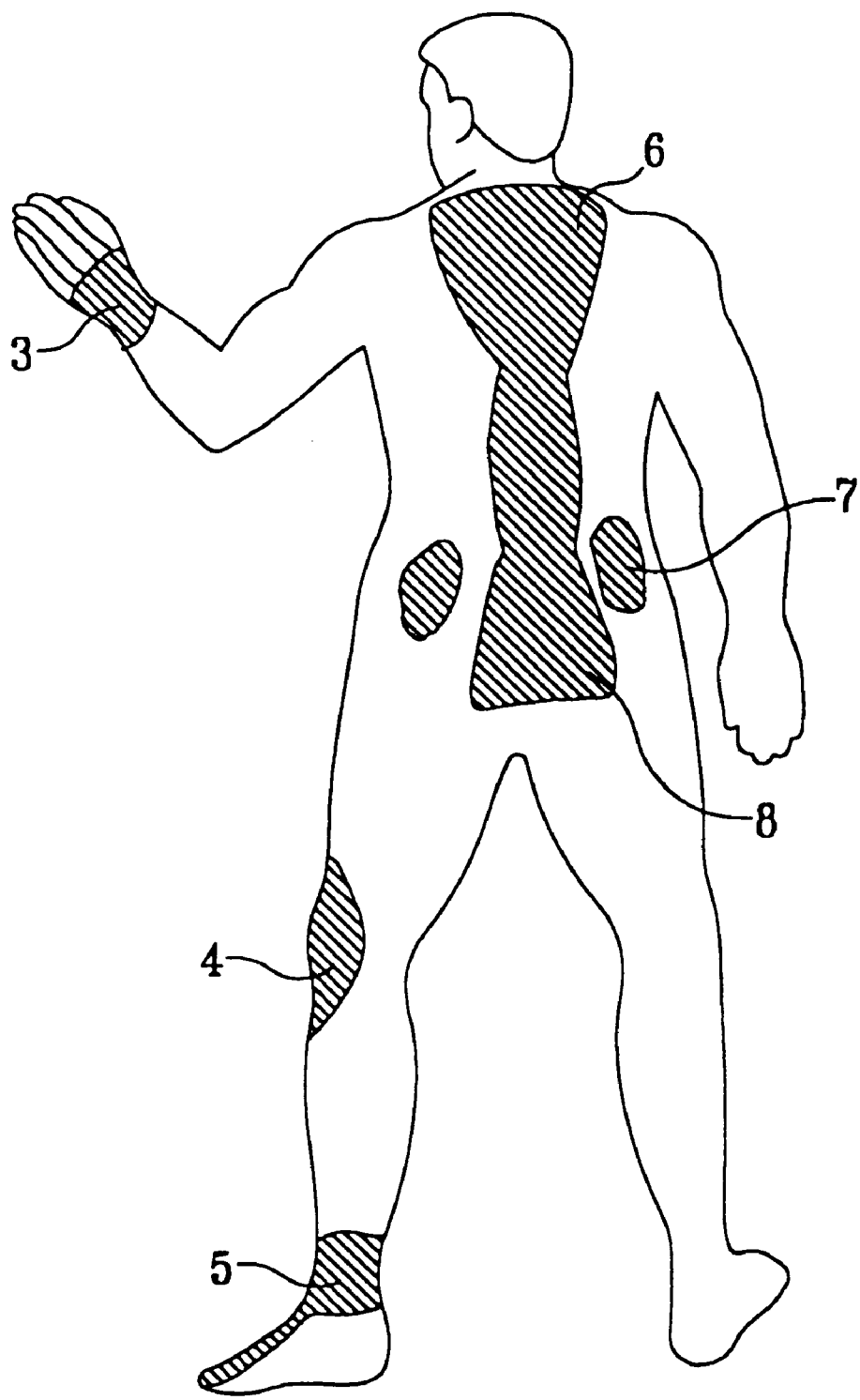
FIG. 2 illustrates the areas of the human body to which compositions of the present invention are to be applied to alleviate the pain associated with arthritis, migraine headaches, muscular aches and strains and neck and back pain and strains.

FIG. 2 also illustrates several applications of the therapeutic compositions of the present invention. For treatment of arthritic pain in the joints, for example in the joints of the hands and wrist area 3, in the knee area 4 and the ankle and foot areas 5, a therapeutic composition of the present invention is applied to these areas of the body as illustrated by the shaded area in FIG. 2.

For arthritic pain, the therapeutic composition preferably comprising 95% oil of oregano, 3% oil of laurel, 2% oil of myrtle (Composition 1 from the Table) or 95% oil of oregano and 5% oil of laurel (Composition 7 from the Table) is gently applied to the illustrated areas. After waiting 5–20 minutes the therapeutic composition is then reapplied in the same manner. The same composition and type of application, however, can be used for any joint aches and strains, as illustrated in reference numerals 3, 4 and 5. For treatment of ailments along the back area, such as migraine headaches and neck stains 6, pulled back muscles 7 and arthritic and general lower back pain 8, the therapeutic composition preferably comprising 90% oil of oregano, 5% oil of laurel, 2% oil of myrtle and 3% olive oil (Composition 2 from the Table) is gently applied to the illustrated areas. After waiting 5–20 minutes the therapeutic composition is then reapplied in the same manner. For migraine headaches, the application of the appropriate therapeutic composition may be extended along the vertebrate, downward towards the middle of the back, if the application along the upper, middle back, as illustrated, is not sufficient to alleviate the pain.

Figure 3:
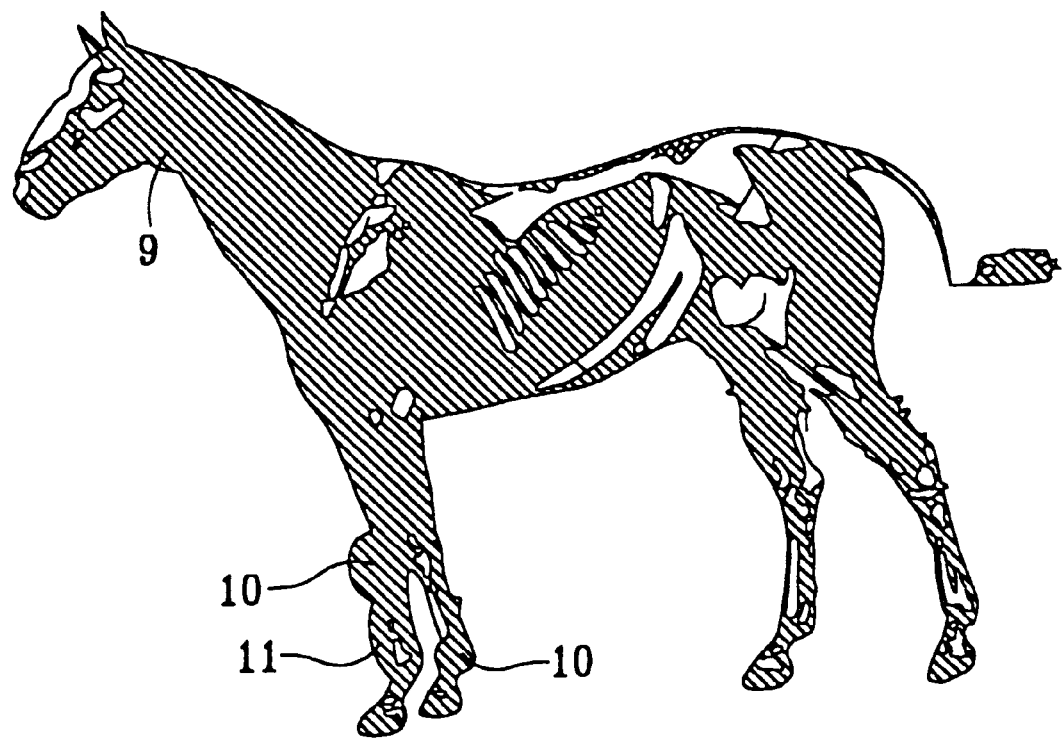
FIG. 3 illustrates the areas of an animal, namely a horse, to which compositions of the present invention are to be applied to alleviate the pain and discomfort associated with upper respiratory, joint and shin ailments.

FIG. 3 illustrates several applications of the present invention with animals, in particular horses. For ailments associated with the neck area, such as non-specific respiratory noises and gurgling 9, the therapeutic composition comprising 35% oil of oregano, 20% oil of laurel, 35% oil of myrtle and 10% olive oil (Composition 4 from the Table) is gently applied to the illustrated areas. After waiting 5–20 minutes the therapeutic composition is then reapplied in the same manner. For inflamed joints, that is, knee or ankle joints 10, the therapeutic composition comprising 80% oil of oregano, 10% oil of laurel, and 10% oil of myrtle (Composition 5 from the Table) is gently applied to the illustrated areas. After waiting 5–20 minutes the therapeutic composition is then reapplied in the same manner. For general shin problems and pain 11, the therapeutic composition comprising 100% oil of oregano (Composition 6 from the Table) is gently applied to the illustrated areas. After waiting 5–20 minutes the therapeutic composition is then reapplied in the same manner. This latter composition is also useful for equine "bucked" shin syndrome.

A characteristic of the topical application of the therapeutic compositions of the present invention includes a general warming sensation at the site of application with occasional and temporary redness of the skin at the applied area. The therapeutic and curative effects of the compositions of the present invention are due to the capacity of these compositions to open blood passages and increase blood flow to area of application, thereby allowing for the body's own pain relievers, such as endorphins which are a group of proteins produced in the body with potent analgesic properties, to more ready access the affected area. Additionally, the herbal oils used in the therapeutic compositions of the present invention have analgesic, anti-inflammatory and decongestive properties, as well as documented antimicrobial activity. In general, these therapeutic compositions are applied from 1–5 times over a course of days, generally with at least a 24 hour period between treatments. Moreover, only a sparing amount of the therapeutic compositions are to be applied to the affected area, just enough to cover the skin at the proximate site of pain or discomfort.

The effectiveness of the topical and locally administered, all herbal, therapeutic compositions described herein is illustrated with the aid of a wealth of clinical information. The following clinical result and case histories illustrate the overall effectiveness of the compositions of the present invention.

EXAMPLE 1

The all herbal composition of the present invention was first used to treat equine shin ailments. In particular, a 2 year old, thoroughbred horse suffering with pain in the legs and shins was treated with the therapeutic composition comprising 100% oil of oregano (Composition 6 from the Table). This composition was gently applied to the affected areas. This application was repeated after 10 minutes. Also, this composition was used with this horse to treat inflamed joints. In both cases, after two separate applications, this horse displayed a significant improvement in his ability to walk and run without noticeable pain and discomfort.

EXAMPLE 2

A 26 year old male suffering from debilitating lower back pain from a bicycle accident was treated with the therapeutic composition comprising 90% oil of oregano, 5% oil of laurel, 2% oil of myrtle and 3% olive oil (Composition 2 from the Table). This composition was applied to the lower back and along the side of this affected area. After the initial application, the subject was able to touch his toes without bending his knees. Prior to an application of the therapeutic composition, the subject had been unable to perform this exercise and had suffered the debilitating effect of the non-specific lower back pain for years.

EXAMPLE 3

A 35 year old female, suffering with an inflamed and swollen knee from an injury incurred while running, was treated with the therapeutic composition comprising 95% oil of oregano, 3% oil of laurel and 2% oil of myrtle (Composition 1 from the Table). This composition was gently applied to the affected area. After waiting 10 minutes, the composition was reapplied. This application was repeated two more times which was sufficient to allow for an apparent complete recovery from the debilitating knee injury.

EXAMPLE 4

A 58 year female previously diagnosed with breast cancer, who had undergone a bone marrow transplant followed by radiation therapy, was left with debilitating pain throughout her body, with particularly intense pain in the neck and shoulder area of the body. In this case, the therapeutic composition of the present invention comprising 95% oil of oregano, 3% oil of laurel and 2% oil of myrtle (Composition 1 from the Table) was applied to the neck and shoulder area. This treatment was repeated three times with 24 hours between the repeated applications. After the first treatment, the subject was feeling less pain, and could move her head from side to side, which she was not able to do before the treatment. By the third treatment, the subject was left feeling pain free in her neck and shoulder areas.

EXAMPLE 5

A 23 male jockey was injured while riding and was suffering from severe neck, shoulder, back and ankle injuries, which caused him only to be able to walk with the aid of crutches. In this case, the therapeutic composition comprising 95% oil of oregano, 3% oil of laurel and 2% oil of myrtle (Composition 1 from the Table) was applied one time directly to the injured areas. Within one hour of the application, the subject was able to walk with much less pain. Several days later, the subject was able to exercise horses, and within a week, the subject was again riding horses. This single treatment, therefore, was able to accelerate the healing process dramatically and decreased it from about two months to one week.

EXAMPLE 6

A 28 year female was suffering from chronic pain caused by inflamed knees. She was also suffering from migraine headaches. This subject had tried various pain medication, acupuncture and chiropractic adjustments with no apparent relief from the pain associated with her chronic ailments. Using the therapeutic composition comprising 95% oil of oregano, 3% oil of laurel, 2% oil of myrtle (Composition 1 from the Table) applied at the affected knee areas, as well as the therapeutic composition comprising 90% oil of oregano, 5% oil of laurel, 2% oil of myrtle and 3% olive oil (Composition 2 from the Table) applied at the middle of the back and back of the neck areas, totally alleviated the pain associated with the ailments. These applications were repeated one time, leaving the subject pain free six months following the last treatment.

EXAMPLE 7

A 25 year old male jockey was thrown from his horse while riding and suffered extreme body soreness and muscular aches. Due to his soft tissue injuries, the subject was not able to walk or ride for eight days following the injury. At this point in time, the subject received treatment to his back with the therapeutic composition comprising 90% oil of oregano, 5% oil of laurel, 2% oil of myrtle and 3% olive oil (Composition 2 from the Table). The subject received only one treatment and subsequently he was able to ride the very next day. Thus, his recuperation process was accelerated by about one month following treatment.

EXAMPLE 8

A 55 year male was suffering from severe, arthritic lower back pain that caused him to be unable to get out of a chair without feeling sharp pain in his lower back. In this case, the therapeutic composition comprising 90% oil of oregano, 5% oil of laurel, 2% oil of myrtle and 3% olive oil (Composition 2 from the Table) was applied to the lower back area. After only one application, the pain was alleviated. Eight months following this single treatment with the therapeutic composition, the subject has remained free of pain.

EXAMPLE 9

A 20 year old female was suffering from severe migraine headaches for about two years. She had been treated with antibiotics which had not helped. The therapeutic composition comprising 90% oil of oregano, 5% oil of laurel, 2% oil of myrtle and 3% olive oil (Composition 2 from the Table) was applied between the shoulder blades and down the vertebrae to the middle of the back. This application was repeated and following the second treatment, the subject apparently no longer suffered from migraine headaches. Six months following the second application of the all herbal composition, the subject had not had a recurrence of the debilitating migraine headaches.

EXAMPLE 10

A 55 year old male had arthritic-like pain in his joints, particularly in the neck area and his knee joints. The therapeutic composition comprising 90% oil of oregano, 5% oil of laurel, 2% oil of myrtle and 3% olive oil (Composition 2 from the Table) was applied to the neck area, with the composition comprising 95% oil of oregano, 3% oil of laurel, 2% oil of myrtle (Composition 1 from the Table) being applied to the affected knee areas. Following one treatment with these compositions, the subject felt much less pain and could move his neck to the left and to the right, which he had not been able to do before the treatment. The treatment to the knees allowed the subject to walk up and down stairs without pain. This type of movement had previously caused the subject to experience pain in his knee joints. This initial treatment was followed by two more like applications, which further reduced any pain associated with the subject's neck and knee joint ailments.

EXAMPLE 11

A 56 year old male had been in a car accident 20 years prior to treatment with the composition of the present invention. This accident had left the subject with severe neck and back ailments. Following the accident, the subject's neck was unable to be held upright, but would tilt to one side. Over this twenty year period, the subject also had to be bedridden periodically due to the intense pain. The numerous medical treatments and medications that this subject received over the twenty year period did little to alleviate the pain. The subject was treated with the therapeutic composition comprising 90% oil of oregano, 5% oil of laurel, 2% oil of myrtle and 3% olive oil (Composition 2 from the Table) applied to the neck area. After this first application, the subject's pain was greatly reduced and she could move her neck and back without too much difficulty. This initial application was repeated two more times. Following the third treatment, the subject was able to turn her head in any direction without pain and could touch her toes also without pain. Both movements previously could not be performed without associated pain and discomfort.

EXAMPLE 12

A 35 year old female who had been an avid horse rider for many years was suffering from non-specific back pain, probably caused by years of riding, as the pull of the horse during riding causes stress in the back. This subject was left with chronic back pain that occurred in the form of spasms. The subject had tried many types of treatments, including drugs and chiropractic treatments. These treatments did not do much to alleviate the chronic, spasmodic back pain. In this case, the therapeutic composition comprising 90% oil of oregano, 5% oil of laurel, 2% oil of myrtle and 3% olive oil (Composition 2 from the Table) was applied to the back area. Within minutes of this single application, the subject was able to stand up straight, which was unusual because she had back spasms prior to the treatment and these back spasms usually required about four days for recovery. Eight months following this single treatment, the subject reported that she had not suffered from any spasmodic back pain.

EXAMPLE 13

A 72 year old female with diagnosed with rheumatoid arthritis had been suffering with the debilitating effects of the disease for approximately two years. Prior to treatment with the compositions of the present invention, the subject's fingers had started to turn and her feet were swollen and inflamed making walking very difficult. In this case, the therapeutic composition comprising 90% oil of oregano, 5% oil of laurel, 2% oil of myrtle and 3% olive oil (Composition 2 from the Table) was applied to the subjects neck, shoulder, hands and feet. Following the initial application, the subject was able to walk with much less pain. After three more like treatments, the subject's fingers began to straighten and associated swelling in the hands and feet was greatly diminished. Without any further medical treatments from her doctors, six months following the all herbal treatment with the compositions of the present invention, the effects from the rheumatoid arthritis have not continued to progress, which is the typical course for this type of ailment.

EXAMPLE 14

A 32 year old female who had been suffering from migraine headaches for several years. The headaches had been occurring on a very frequent basis. Moreover, the subject was constantly taking aspirin to alleviate her severe pain. Although her physician offered stronger prescription medications, the subject did not want to take these drugs because of possible side effects. The subject received three treatments with the therapeutic composition of the present invention comprising 90% oil of oregano, 5% oil of laurel, 2% oil of myrtle and 3% olive oil (Composition 2 from the Table). The herbal composition was applied to the back of her neck downward towards the center of the back. Following these treatments, the subject reported a decrease in the occurrence of the migraine headaches with only minor pain associated with mild infrequent headaches.

EXAMPLE 15

A 58 year old male had been suffering with arthritic knees for approximately 15 years. He was treated with the therapeutic composition comprising 95% oil of oregano, 3% oil of laurel, 2% oil of myrtle (Composition 1 from the Table) which was applied to the affected knees. Three years subsequent to this single treatment, the subject had not experienced pain in his knees.

EXAMPLE 16

A 42 year old male who was suffering from injuries resulting from a fall from a horse. His injuries affected his back and left shoulder and caused him to be unable to ride horses due to the severe pain. This subject was treated with the therapeutic composition comprising 90% oil of oregano, 5% oil of laurel, 2% oil of myrtle and 3% olive oil (Composition 2 from the Table) applied directly to the injured areas. After one treatment, the pain in his back and shoulder had subsided. This treatment was repeated one more time, and the subject reported that he was able to ride within a day of the second treatment, thus accelerating his recovery by approximately one month. On a subsequent occasion, the subject was again injured while riding and suffered a hairline fracture of his left heel which caused him much pain while walking. After a single treatment comprising 95% oil of oregano, 3% oil of laurel, 2% oil of myrtle (Composition 1 from the Table) which was applied directly to the affected heel, the pain had greatly subsided and the subject could walk without pain.

EXAMPLE 17

A 42 year old male had been suffering from migraine headaches and was being treated by a physician with injections and other medications to help alleviate the pain and recurrence of the headaches. This subject was treated three times with the therapeutic composition comprising 90% oil of oregano, 5% oil of laurel, 2% oil of myrtle and 3% olive oil (Composition 2 from the Table) applied to the back the neck and middle back. In the year following the treatments, the subject reported that he had not experienced any migraine headaches.

EXAMPLE 18

A 35 year old male had undergone surgery due problems with the ligaments in one knee. Following the surgery, he had experienced swelling at the site of the surgery which caused him pain and discomfort. Following a single treatment with the therapeutic composition comprising 90% oil of oregano, 5% oil of laurel, 2% oil of myrtle and 3% olive oil (Composition 2 from the Table) applied directly to his knee, the swelling in his knee, which had persisted for approximately 3 years following the surgery, subsided in one day.

EXAMPLE 19

A 36 year old female had been suffering with migraine headaches for several years and was being treated by her physician. Her medical treatments did not provide any relief from the pain and the recurrence of migraines. This subject was treated three times with the therapeutic composition comprising 90% oil of oregano, 5% oil of laurel, 2% oil of myrtle and 3% olive oil (Composition 2 from the Table) applied directly to the back of the neck and middle back areas. Following these treatments, the subject reported that she had not experienced any migraine headaches.

EXAMPLE 20

A 48 year old male was suffering from chronic bronchitis. The therapeutic composition comprising 60% oil of oregano, 20% oil of laurel, 15% oil of myrtle and 5% olive oil (Composition 3 from the Table) was applied gently to the chest area. After 15 minutes, the subject started to vigorously cough up the mucous congested in his lungs. The therapeutic composition was then reapplied. The following day, the subject experienced a clearing of the remaining congestion. This treatment was repeated one more time. One year subsequent to the treatments, the subject has not had a recurrence of the bronchial episodes.

EXAMPLE 21

A 34 year old male was injured in physical brawl. He had experienced a blow to the right side of his face. This blow caused him not to be able to move the muscles on the right side of his face, including the muscles in his right eye. For two months, he was unable to close his right eye. The therapeutic composition comprising 60% oil of oregano, 20% oil of laurel, 15% oil of myrtle and 5% olive oil was applied gently (Composition 3 from the Table) along the right side of his face, around the ears and then downward along the right shoulder. After this initial treatment, the subject was able to move the muscles in his face for the first time in two months. The treatment was repeated the next day. Following this second treatment, the subject completely recovered from his injuries.

The foregoing clinical results clearly indicate that the all herbal composition described herein comprising at least the oil of oregano, oil of laurel and oil of myrtle possesses marked utility, effectiveness and reliability when applied topically to relieve the pain and discomfort associated with arthritis, migraine headaches, bronchitis, soft tissue injures, muscular aches and strains, and neck and back strains. Moreover, a composition comprising only the oil of oregano proved useful in alleviating certain ailments in horses.

Although the therapeutic compositions herein disclosed as certain formulae used for certain ailments, it is to be noted that changes may be made to the compositions and applications described, such as the relative amounts of the essential oil, applications areas, amounts to be applied and time of applications, without departing from the scope of the invention. Thus, the subject matter described herein is merely illustrative of what is claimed as the invention.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Also, any element in a claim that does not explicitly state "means" for performing a specified function or "step" for performing a specified function, should not be interpreted as a "means" or "step" clause as specified in 35 U.S.C. §112.

What is claimed is:

1. A therapeutic composition to be used topically for alleviating the pain and discomfort associated with arthritis, migraines, bronchitis, facial paralysis or numbness, soft tissue injures, muscular aches and strains, and neck and back strains comprising:

an effective amount of oil derived from oregano from about 60–95 percent volume;

an effective amount of oil derived from green laurel leaves from about 3–20 percent volume; and an effective amount of oil derived from green myrtle leaves from about 0–15 percent volume, wherein the oregano, laurel and myrtle oils are combined to yield the therapeutic, topical composition.

2. The therapeutic composition of claim 1, wherein the oregano oil, the laurel oil and the myrtle oil are obtained by distillation to yield an oregano distillate, a laurel distillate and a myrtle distillate.

3. The composition of claim 2, wherein the oregano distillate, the laurel distillate and the myrtle distillate are derived from plants grown in Cyprus, Crete or Greece.

4. The composition of claim 2, wherein the oregano distillate is derived from dried leaves, stems and seeds of an oregano plant, the laurel distillate is derived from the green leaves of a laurel plant, and the myrtle distillate is derived from the green leaves of a myrtle plant.

5. The therapeutic composition of claim 1, wherein the oregano oil, the laurel oil and myrtle oil are obtained by extraction.

6. The therapeutic composition of claim 1, wherein olive oil is added to the mixture from 2–10 percent volume.

7. The topically administrable therapeutic composition of claim 1 in the form of a cream, lotion ointment or salve.

8. A method of making a therapeutic composition for topical use in alleviating the discomfort associated with arthritis, migraines, bronchitis, soft tissue injures, facial paralysis or numbness, muscular aches and strains, and neck and back strains in humans and upper respiratory, joint and shin ailments in animals comprising:

distilling or extracting dried leaves, stems and seeds of an oregano plant in water to form an oil;

distilling or extracting green leaves of a laurel plant in water to form an oil;

distilling or extracting green leaves of a myrtle plant in water to form an oil;

mixing the oregano oil from about 60–95% volume, the laurel oil from about 3–20% volume, and the myrtle oil from 0–15% volume to form the therapeutic, topical composition.

9. The method of claim 8, further comprising separately drying the laurel distillate, or extract the myrtle distillate or extract and the oregano distillate or extract to remove water or other solvents from the distillates or extracts prior to mixing.

10. The method of claim 8, wherein the oregano distillate or extract are derived from dried leaves, stems and seeds of an oregano plant, the laurel distillate is derived from the green leaves of a laurel plant, and the myrtle distillate or extract are derived from the green leaves of a myrtle plant.

11. The method of claim 8 further comprising adding up to 10 percent by volume of olive oil to the therapeutic composition.

12. A method of alleviating the discomfort or pain associated with arthritis, migraines, bronchitis, soft tissue injures, facial paralysis or numbness, muscular aches and strains, and neck and back strains comprising:

applying the therapeutic, topical composition of claim 1 topically to the proximate area of discomfort or pain with an amount of the therapeutic composition effective to relieve the discomfort or pain.

13. The method of claim 12, further comprising reapplying the therapeutic composition of claim 1, after waiting 5–20 minutes following an initial application.

14. The method of claim 13, wherein the initial application and re-application are repeated 2–5 times with at least a 24 hour interval between treatments.

15. A therapeutic composition for topical application in alleviating the discomfort of upper respiratory, joint and shin ailments in horses comprising:

an oregano distillate or extract obtained from dried leaves, stems and seeds;

a laurel distillate or extract obtained from green laurel leaves; and a myrtle distillate or extract obtained from green myrtle leaves, to yield an oil of oregano, an oil of laurel and an oil of myrtle wherein the composition comprises a mixture of the oil of oregano from 35–95 percent volume, the oil of laurel from 10–20 percent volume and the oil of myrtle from 0–35 percent volume.

16. The therapeutic composition of claim 15, wherein up to 10 percent of the total volume of the composition comprises olive oil.

17. The topically administrable therapeutic composition of claim 15 in the form of a cream, lotion, ointment or salve.

18. A method of alleviating the discomfort or pain associated with upper respiratory, joint and shin ailments in horses comprising:

applying topically to a horse in need at the proximate area of discomfort or pain with an amount of the therapeutic composition of claim 15 effective to relieve the discomfort or pain.

19. The method of claim 18, further comprising reapplying the therapeutic composition of claim 1 after waiting 5–20 minutes following an initial application.

20. A therapeutic composition for use in alleviating the pain and discomfort associated with arthritis, migraines, bronchitis, soft tissue injures, facial paralysis or numbness, muscular aches and strains, and neck and back strains comprising:

an oily oregano distillate;

an oily laurel distillate; and an oily myrtle distillate, wherein the composition comprises a mixture of the oregano distillate from 60–95 percent volume derived from leaves, stems and seeds, the laurel distillate from 3–20 percent volume derived from green laurel leaves and the myrtle distillate from 2–15 percent volume derived from green myrtle leaves, and wherein all the distillates of the therapeutic composition are derived from plants grown in Cyprus, Crete or Greece.

21. The therapeutic composition of claim 20, wherein olive oil is added to the mixture from 2–10 percent volume.

* * * * *